United States Patent [19]
Kahn et al.

[11] Patent Number: 5,772,600
[45] Date of Patent: Jun. 30, 1998

[54] COHERENT PATTERN IDENTIFICATION IN NON-STATIONARY PERIODIC DATA AND BLOOD PRESSURE MEASUREMENT USING SAME

[75] Inventors: Alan R. Kahn, Minneapolis, Minn.; Dennis E. Bahr, Middleton, Wis.; Kurt W. Allen, Minneapolis, Minn.

[73] Assignee: B.P. Sure, L.L.C., Madison, Wis.

[21] Appl. No.: 665,362

[22] Filed: Jun. 17, 1996

[51] Int. Cl.$^6$ .................................................. A61B 5/02
[52] U.S. Cl. ........................................ 600/494; 600/513
[58] Field of Search ................................. 128/670, 680, 128/681, 682

[56] References Cited

U.S. PATENT DOCUMENTS

| | | |
|---|---|---|
| 3,773,033 | 11/1973 | Rodbard et al. . |
| 4,005,701 | 2/1977 | Aisenberg et al. . |
| 4,313,445 | 2/1982 | Georgi . |
| 4,396,018 | 8/1983 | Sibley . |
| 4,408,614 | 10/1983 | Weaver et al. . |
| 4,592,365 | 6/1986 | Georgi . |
| 4,649,929 | 3/1987 | Weaver et al. . |
| 4,819,654 | 4/1989 | Weaver et al. . |
| 4,938,227 | 7/1990 | Niwa et al. . |
| 5,031,630 | 7/1991 | Hirano et al. . |
| 5,135,003 | 8/1992 | Souma . |
| 5,337,750 | 8/1994 | Walloch . |
| 5,392,781 | 2/1995 | Phillipps et al. . |
| 5,649,535 | 7/1997 | Voith . |

OTHER PUBLICATIONS

Kim–Gau Ng & Carolyn F. Small, "Survey of Automated Noninvasive Blood Pressure Monitors", J. Clinical Engineering, vol. 19, No. 6, pp. 452–475, Nov./Dec. 1994.

*Primary Examiner*—Scott M. Getzow
*Attorney, Agent, or Firm*—Foley & Lardner

[57] ABSTRACT

A method and apparatus for automatically recognizing meaningful patterns in non-stationary periodic data is provided. The invention may be used in making measurements of physiological phenomena, such as arterial blood pressure, wherein data of interest is undergoing small changes in timing and magnitude in succeeding cycles, and wherein noise artifacts are detected along with the data of interest. Data points of interest are identified by grouping all received data points into family groups of multi-dimensional data points wherein each data point in the family group has dimensional values similar to at least one other data point in the family. The present invention may preferably be employed for the determination of a patient's systolic and diastolic blood pressure levels. For this application, the data points include a time dimension value corresponding to the delay time between an ECG signal and the detection of a potential blood pressure sound by a microphone placed in an inflatable cuff on the arm of a patient, and a magnitude dimension value corresponding to the cuff pressure at the time of the potential blood pressure sound detection. Data points are collected for a series of cuff pressures ranging from above the systolic blood pressure level of the patient to below the diastolic blood pressure level of the patient. The highest and lowest pressures of data points in the family containing the largest number of data points are used to derive the systolic and diastolic blood pressure levels of the patient, respectively.

22 Claims, 8 Drawing Sheets

COHERENT PATTERN IDENTIFICATION IN NON-STATIONARY PERIODIC DATA AND BLOOD PRESSURE MEASUREMENT USING SAME

FIELD OF THE INVENTION

This invention pertains generally to methods and devices for identifying coherent patterns in non-stationary periodic data, and more particularly to methods and devices for recognizing meaningful patterns in non-stationary periodic data for measuring physiological phenomena, including measuring a patient's blood pressure.

BACKGROUND OF THE INVENTION

Due to the cyclic nature of many physiological processes, such as respiration and heart beat, periodic data is often encountered in the measurement of physiological phenomena. In some cases, the data used for the physiological measurement changes incrementally in consecutive cycles. Thus, data representative of physiological events, though substantially periodic, may occur at somewhat different times and with different magnitudes in consecutive cycles. This type of data is known as non-stationary periodic data.

An example of the use of non-stationary periodic data for making a physiological measurement is in the indirect measurement of a patient's blood pressure. A common method of measuring a patient's blood pressure utilizes an inflatable cuff wrapped around the upper arm of the patient. As the cuff is inflated, pressure is applied to a brachial artery in the patient's arm beneath the cuff. The blood pressure in the brachial artery is not constant, but varies with respect to the patient's heart beat cycle. Following a contraction of the heart to pump blood through the patient's circulatory system, the blood pressure in the artery reaches a maximum level known as the systolic blood pressure level. The lowest blood pressure level reached between heart beats is known as the diastolic blood pressure level. When the pressure level in the cuff exceeds the systolic blood pressure level, the brachial artery is forced closed throughout the heart beat cycle. As pressure is released from the cuff, the pressure in the artery is reduced to a level below the systolic blood pressure level, but higher than the diastolic blood pressure level. At this pressure level, the brachial artery is forced opened and closed during each heart beat cycle as the blood pressure in the artery first exceeds the cuff pressure and then falls below the cuff pressure. The opening "snap" of the artery following each heart beat causes low frequency blood pressure sounds to be produced. The turbulent flow of blood through the artery after the artery snaps open also produces sounds, known as Korotkoff sounds. Korotkoff sounds and low frequency blood pressure sounds can be detected by sound pick-ups, such as a stethoscope or a microphone, placed on the patient's arm near or under the cuff. When the cuff pressure is reduced to below the diastolic blood pressure level, the artery will remain open throughout the heart beat cycle, and blood pressure sounds will cease to be produced. Thus, a patient's systolic and diastolic blood pressure levels can be determined from the highest cuff pressure at which blood pressure sounds are detectable and the lowest cuff pressure at which blood pressure sounds are detectable, respectively. This method of determining a patient's blood pressure is known as an auscultatory method.

For manual measurement of a patient's blood pressure using the auscultatory method, where a stethoscope is used to detect Korotkoff sounds, accurate measurement of a patient's blood pressure is highly dependent on the skill and hearing ability of the operator. Thus, automatic blood pressure monitoring systems have been developed to both automate the blood pressure monitoring process and to reduce the dependency of an accurate blood pressure measurement on human judgment. Automatic blood pressure monitoring systems typically employ an automatically inflatable and deflatable cuff, with one or more microphones placed on the patient's arm under the cuff for detecting the blood pressure sounds. The microphones pick up Korotkoff sounds and blood pressure sounds produced by the periodic opening of the brachial artery, however, they are also highly susceptible to picking up noise caused by the motion of the patient, such as during exercise or shivering, and ambient environmental noise, such as from a vehicle in which a patient is being transported. Thus, automatic blood pressure monitoring systems that merely automate the auscultatory blood pressure measurement method typically are not capable of providing usable blood pressure measurements in the presence of significant noise that interferes with the detection of blood pressure sounds.

Various systems and methods have been developed to improve the performance of automatic blood pressure monitoring systems by attempting to separate useful blood pressure sound signals from noise signals picked up by the blood pressure monitoring system microphones. One such method includes band pass filtering of the microphone signals to select the frequency components of blood pressure sounds and to reject frequency components characteristic of noise. Other systems involve placing two microphones on a patient, separated by a distance such that a blood pressure sound signal is picked up out of phase at each microphone, and subtracting and adding the out of phase microphone signals to enhance the signal of interest and to obtain signal and noise threshold values. In another system, two microphones are placed on a patient's arm, one upstream from the other, such that a signal picked up by the upstream microphone opens a time gate window in which the downstream microphone "listens" for the occurrence of an expected blood pressure sound. These two-microphone methods for extracting useful blood pressure sound data from microphone signals rely on the fact that a low frequency blood pressure sound will be picked up by two separated microphones at different times and out of phase, whereas noise signals, travelling at the speed of sound, will be picked up substantially simultaneously and in phase by each separated microphone.

Another method of deriving useful blood pressure sound information from microphone signals in a noisy environment relies on the fact that the time of the occurrence of blood pressure sounds in the arm of a patient, at a series of cuff pressures, with respect to the time of the heartbeat, forms a coherent pattern of non-stationary periodic data that can be identified. An electrocardiogram (ECG) may be used to detect the QRS wave complex corresponding to each heartbeat cycle. A blood pressure sound will be produced in the upper arm of the patient after a time delay following the ECG signal. Under steady circumstances, the blood pressure sound will appear at roughly the same time after the ECG signal for each heart beat cycle. However, as the pressure in the arm cuff is reduced during a blood pressure measurement cycle, the time delay of the appearance of blood pressure sounds following the ECG signal will undergo relatively small changes. For consecutive pulses at successively lower cuff pressures, the delay time will generally decrease, but not consistently, on every beat. A plot of the delay times versus cuff pressures over a blood pressure monitoring cycle will form a coherent pattern. Noise signals that are detected by the microphones will appear as artifacts in the same plot. However, if the coherent data pattern, representing blood pressure sounds, can be distinguished from the noise artifacts, the systolic and diastolic blood pressure levels of a patient can be accurately determined from the points in the coherent pattern corresponding to the highest cuff pressure and lowest cuff pressure, respectively.

A method for identifying the coherent pattern of the blood pressure sound data is described in U.S. Pat. No. 4,408,614, to Weaver, et al. In this patent, data points in a plot of cuff pressure versus delay time between the detection of potential blood pressure sounds and an ECG signal are grouped together using a chaining operation. By this method, data points are considered to belong to the same group if they do not exceed a certain threshold distance from a line corresponding to the expected slope (related to the systolic slope) of the plot projected through other data points in the same group. After the chaining operation is complete, the group that includes the greatest number of data points is selected as the group containing data points corresponding to blood pressure sound detections, with the data points in other groups representing artifacts. Systolic and diastolic blood pressure levels can then be calculated from the data points in the selected group.

SUMMARY OF THE INVENTION

The present invention provides a method and apparatus for automatically recognizing meaningful patterns in non-stationary periodic data wherein the data is undergoing small changes in timing and magnitude with each succeeding cycle. The present invention is particularly applicable to the identification of coherent patterns in non-stationary periodic data that is frequently encountered when making measurements of phenomena in physiology and clinical medicine, such as blood pressure measurements. The present invention specifically provides for the identification of coherent patterns in data that is contaminated with significant levels of noise artifacts.

In accordance with the present invention, the identification of coherent data patterns is based upon the similarity of data points in at least two dimensions. These are typically magnitude and time dimensions. Similar points are grouped together into groups called families. Data points that are not similar to other data points in the dataset are not grouped together. Ungrouped data points are called orphans. In very noisy situations, more than one family group may be identified. The present invention identifies the family group with the largest number of data points as containing the data points of interest.

Each data point in a set of data points to be grouped is multi-dimensional. Each data point in the data set typically includes at least a time dimension value, corresponding to a time dimension value of a detected phenomenon, and a magnitude dimension value, corresponding to a magnitude dimension value of a detected phenomenon. For data points in a set of data points, two data points are considered "related" to each other, and thus are grouped into the same family, if their dimension values are "similar". Similar data points are thus "close" to each other in an x-dimensional graph. For example, two data points $d^1_x$ and $d^2_x$ in x-dimensional space may be considered similar if $|d^1_x - d^2_x| < threshold_x$, where $threshold_x$ is an x-dimensional number that defines a maximum distance in each dimension that the two points $d^1$ and $d^2$ can be away from each other and still be related. Other more complicated similarity functions may also be used.

If data points $d^1$ and $d^2$ are related, and data points $d^2$ and $d^3$ are related, then data points $d^1$ and $d^3$ are related. Thus, a family of data points includes all data points in the dataset such that each data point in the family has similar dimension values to at least one other data point included in the family. A family may be defined as any group of at least a selected number of related data points. Data points that are not members of a family are orphans. The data points of interest are defined to be the data points in the family which, after all data points have been assigned to families or defined as orphans, includes the most data points.

The present invention is particularly suited to the measurement of a patient's systolic and diastolic blood pressure levels in the presence of significant levels of noise. In this application of the present invention, the data points are two dimensional data points that may be mapped into a two dimensional Cartesian coordinate space. The two dimensional values defining each data point are the time delay between an ECG signal and the detection of a potential blood pressure sound by a microphone placed on the arm of a patient underneath an inflatable cuff, in the time dimension, and the cuff pressure, in the magnitude dimension. If two data points occur within a delay time threshold value of each other, and are within a pressure threshold value of each other, they are similar and related, and are grouped together in the same family. At the end of a blood pressure monitoring cycle, the data points in the family having the largest number of data points are selected as the data points of interest, representing blood pressure sound detections. Data points in other families, and orphan data points, represent noise artifacts. The patients' blood pressure levels may be accurately determined from the selected data points of interest.

An automatic blood pressure monitoring system employing the present invention includes an inflatable cuff wrapped around the upper arm of a patient, and a microphone placed on the arm of the patient underneath the cuff. The microphone may generally be fixed within the cuff. A pressure controller is used to increase the cuff pressure to a level exceeding the maximum probable systolic blood pressure level of the patient, causing a brachial artery in the patient's arm beneath the cuff to be forced closed. The pressure in the cuff is then gradually reduced in a continuous or step-wise fashion. When the cuff pressure is reduced below the systolic blood pressure level of the patient, blood pressure sounds will be produced by the opening of the artery each heart beat cycle. These blood pressure sounds, along with Korotkoff sounds and noise artifacts caused by movement or shivering of the patient, or ambient noise from the patient's environment, will be picked up by the microphone. An ECG signal is also detected, as the cuff pressure is being gradually reduced. As potential blood pressure sounds are picked up by the microphone, the delay time between the potential blood pressure sound detection and the occurrence of the last previous ECG signal, along with the corresponding cuff pressure, measured using a pressure transducer, are collected as data points in memory. Each data point in memory is thus a two dimensional variable having a time dimension value corresponding to the delay time between the ECG signal and the microphone signal detection, and a magnitude dimension value corresponding to the cuff pressure at the potential blood pressure sound detection time. Each time a new data point is added to the dataset during a blood pressure monitoring cycle, the entire set of data points may be grouped into families of similar data points that are separated in the time and magnitude dimensions by less than selected delay time and pressure thresholds, respectively. Preferably, the data points in the family including the largest number of data points are displayed in a two dimensional plot on a blood pressure monitoring system display screen. As data points are added to the displayed family during the blood pressure measurement cycle, they are also displayed. If another family grows to include more data points than the displayed family, the displayed family is erased from the display screen and replaced by the data points from the new, larger, family.

In a typical blood pressure measurement cycle, blood pressure sound detections will form a curve made up of fifteen to twenty data points. Even in highly noisy environments, families including data points corresponding to noise artifacts usually contain less than five data points. Thus, blood pressure sound detections almost always form data points in the family including the largest number of data points. At the end of the blood pressure measurement cycle, after all data points have been grouped into families or defined as orphans, data points in the family including the largest number of data points are selected as the data points of interest. The data points of interest corresponding to the highest and lowest cuff pressure levels are used to determine the systolic and diastolic blood pressure levels of the patient, respectively.

The present invention thus makes possible the identification of a coherent data point pattern, corresponding to blood pressure sounds, in the presence of large numbers of artifact data points caused by noise interference, and the accurate determination of a patient's blood pressure levels from the data in the identified pattern. It does not matter in which order the data points to be analyzed are gathered. Thus, data points can be gathered either during the inflation or the deflation of the inflatable cuff. As a patient moves the arm on which the inflatable cuff is placed, wide pressure fluctuations in the cuff will be produced. Potential blood pressure sounds detected during these periods of pressure fluctuation represent additional data points that are included in the data set and that may be included by the present invention into the identified coherent pattern of blood pressure sounds. Thus, data points generated for any given heart beat may contain valid blood pressure sound information, and are used by the method of the present invention to fill in the coherent pattern of interest. It is important that many data points be acquired at various cuff pressure levels extending from above the maximum probable systolic blood pressure level to below the minimum probable diastolic blood pressure level, for an accurate determination of systolic and diastolic blood pressure levels to be made using the present invention.

In an alternative embodiment of the present invention, signals from two microphones are used to generate data points from which a coherent pattern may be identified. The two microphones are placed a fixed distance apart, underneath an inflatable blood pressure cuff, such that a low frequency blood pressure sound will be picked up approximately 180° out of phase by each microphone. The cuff is inflated and deflated to apply various pressure levels to an artery, from above the systolic blood pressure level to below the diastolic blood pressure level of the patient. At each cuff pressure level, the signals from the two microphones are analyzed to generate a three dimensional data point. These dimensions include the distance between the peaks of the microphone signals (time dimension), the ratio of the amplitudes of the two microphone signal peaks (magnitude dimension), and the ratio of the widths of the two microphone signal peaks (time dimension). The data points are then grouped into families in accordance with the present invention, with data points having similar values in all three dimensions being grouped together in the same family. The data points in the family including the largest number of data points are identified as the data points of interest from which the systolic and diastolic blood pressure levels of the patient may be determined.

Further objects, features, and advantages of the invention will be apparent from the following detailed description taken in conjunction with the accompanying drawings.

BRIEF DESCRIPTION OF TEE DRAWINGS

DETAILED DESCRIPTION OF THE INVENTION

The present invention provides for the identification of coherent patterns in non-stationary periodic data. Non-stationary periodic data includes information that is undergoing small changes in timing and magnitude with each succeeding cycle. This type of data is frequently encountered when making measurements of phenomena in physiology and clinical medicine. The present invention will, therefore, be found particularly applicable to making physiological measurements wherein coherent data patterns of interest need to be identified in datasets containing significant numbers of artifact data points caused by noise or other interference. The following description describes the present invention in detail using an exemplary application of the invention in an automatic method and apparatus for determining a patient's blood pressure. It should be understood, however, that the present invention may also be applied to methods and devices for making other types of physiological measurements. In general, the present invention may be used in any situation requiring the identification of a coherent non-stationary periodic data pattern in a dataset including data points of interest and artifact data points from which the coherent pattern must be distinguished.

Figure 1:
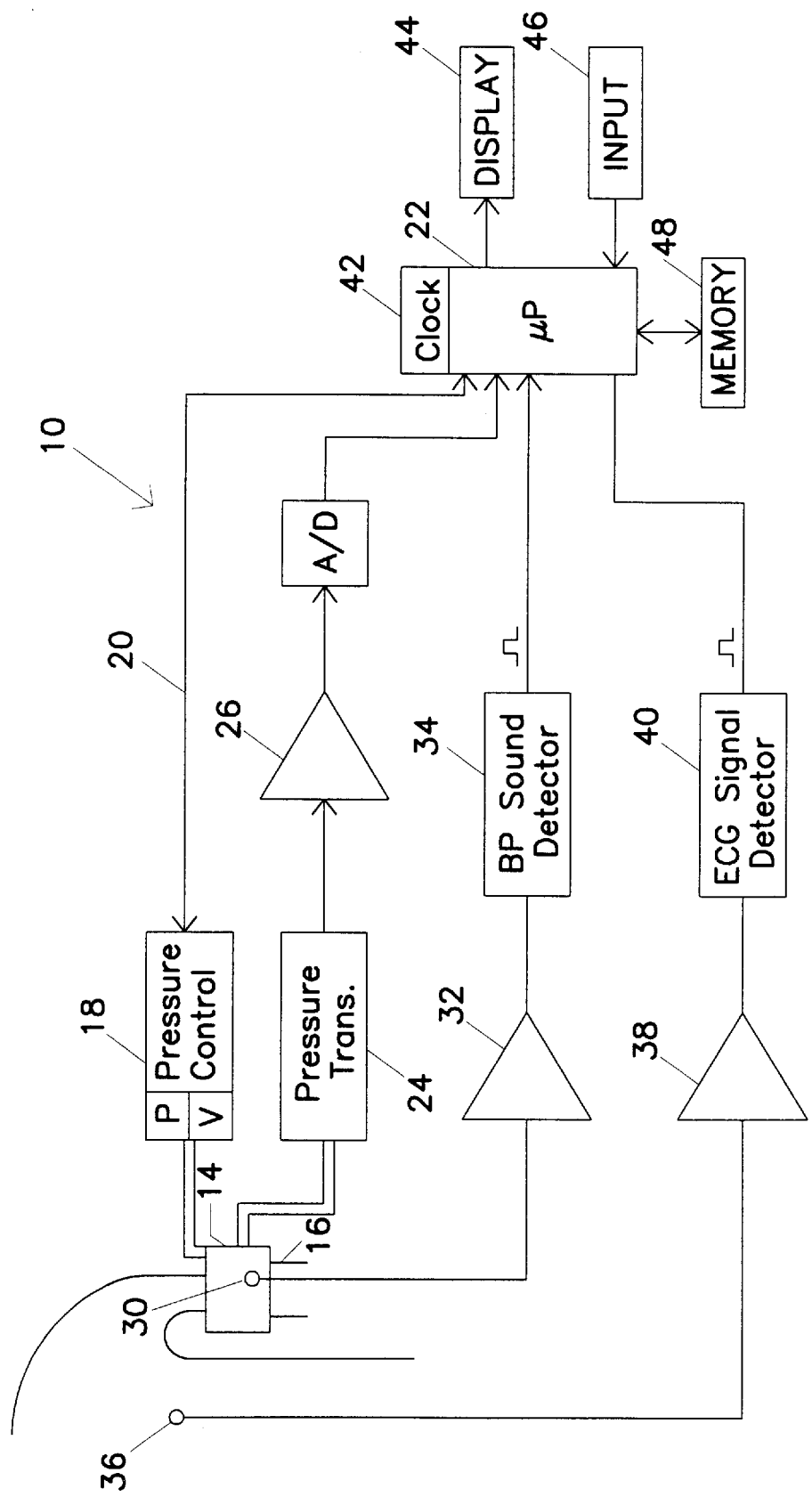
FIG. 1 is a schematic block diagram of an automatic blood pressure monitoring system employing coherent pattern identification in accordance with the present invention.

An exemplary automatic blood pressure monitoring system 10, in which the present invention may be employed, is illustrated in FIG. 1. The blood pressure monitoring system 10 is used to automatically determine and display the systolic and diastolic blood pressure levels of a patient 12. The blood pressure monitoring system 10 includes an automatically inflatable cuff 14 that is wrapped around a limb of the patient 12, such as the patient's upper arm 16. A pressure controller 18 is used to inflate and deflate the cuff 14 to apply pressure to the patient's arm 16. The pressure controller 18 may be of a conventional design used in commercially available automatic blood pressure monitoring systems. The pressure controller 18 may thus include a pump P for inflating the cuff 14, and one or more valves V for slowly and/or rapidly deflating the cuff 14 to reduce the cuff pressure. The pressure controller 18 preferably inflates or deflates the cuff 14 to selected pressure levels in response to control signals on a line 20 from a system microprocessor 22 that controls the blood pressure monitoring cycle.

The pressure in the cuff 14 is sensed by a pressure transducer 24. The pressure transducer 24, which may be of conventional design, produces an analog pressure signal that may be filtered to remove unwanted noise and amplified by an analog amplifier 26. The resulting amplified analog cuff pressure signal is preferably converted to a digital signal, by an analog-to-digital converter 28, that is provided to the microprocessor 22. It is apparent that the analog-to-digital converter 28 may be implemented as a separate component, as illustrated, or as an integral part of the microprocessor 22. The system microprocessor 22 uses the digital cuff pressure signal to monitor the cuff pressure to generate the control signals that are provided on the line 20 to the pressure controller 18 to instruct the pressure controller 18 to inflate or deflate the cuff 14 to a desired pressure level. The digital cuff pressure signal is also used by the microprocessor 22 to determine the patient's systolic and diastolic blood pressure levels employing a coherent pattern identification method in accordance with the present invention, as will be described in more detail.

With the cuff 14 attached to the upper arm 16 of the patient 12, the cuff 14 is inflated by the pressure controller 18 to a pressure level above the patient's maximum probable systolic blood pressure level. This causes a brachial artery located in the patient's arm 16 below the cuff 14 to be forced closed. The cuff pressure is then gradually reduced by the pressure controller 18. As the cuff pressure is reduced to below the systolic blood pressure level, the artery beneath the cuff will open and close during each heart cycle as the patient's blood pressure first exceeds and then falls below the cuff pressure. The opening "snap" of the artery causes a blood pressure sound to be produced each cycle. Other sounds are produced by the turbulent flow of blood in the artery following the opening of the artery. A microphone 30, placed on the patient's arm 16 beneath the downstream end of the cuff 14 and over the brachial artery, picks up these blood pressure sounds. The microphone 30 also picks up unwanted noise caused by patient movement, such as during exercise or shivering, and ambient noise from the patient's environment, such as from an ambulance or helicopter in which the patient is being transported. The microphone 30 may be implemented using any conventionally designed device for picking up sound signals and producing a corresponding electrical microphone signal, including a piezoelectric sound transducer, and is preferably fixed in the cuff 14.

The microphone signal, including both blood pressure sounds of interest and unwanted noise, is amplified by an amplifier 32 and provided to a blood pressure sound detector 34. The blood pressure sound detector 34 outputs a pulse, step, or other signal that is provided to the microprocessor 22 when the blood pressure sound detector 34 detects that a potential blood pressure sound has been picked up by the microphone 30. The blood pressure sound detector 34 thus provides an initial filtering of the microphone signal in an attempt to distinguish blood pressure sounds of interest from unwanted noise signals.

The blood pressure sound detector 34 may be implemented in various manners, having correspondingly various levels of effectiveness and complexity. The blood pressure sound detector 34 may output a signal indicating the detection of a potential blood pressure sound each time a microphone signal exceeding a selected threshold is received. The blood pressure sound detector 34 may provide for filtering of the microphone signal using a band pass filter having a pass band corresponding to the characteristic frequencies of the low frequency blood pressure sound signal, e.g., 30 Hz–80 Hz. A potential blood pressure sound detection may then be indicated by the blood pressure sound detector 34 when this filtered signal exceeds a selected threshold. This will result in fewer pulses being generated by the blood pressure sound detector 34 that result from noise in the microphone signal rather than the detection of true blood pressure sounds.

Other much more complicated schemes may also be used to implement the blood pressure sound detector 34. For example, a two microphone blood pressure sound detection system may be used wherein two microphones placed under the inflatable cuff 14 are separated by a distance such that blood pressure sounds propagating down the arm 16 are picked up out of phase by each microphone and noise, traveling at the speed of sound, is picked up simultaneously and in phase by each microphone. The signals from each microphone may then be subtracted and/or added to each other to enhance the signal of interest and to derive signal and noise threshold levels. Similarly, two microphones may be placed on the patient's arm underneath the cuff 14 with one microphone placed upstream from the other. The upstream microphone may then be used to generate a time gate for the downstream microphone, causing the downstream microphone to "listen" for an expected blood pressure sound propagating down a patient's arm. Another method for detecting blood pressure sounds using two microphones is described in a co-pending patent application Ser. No. 08/665,286 entitled "METHOD AND APPARATUS FOR DETECTING BLOOD PRESSURE BY BLOOD PRESSURE SOUNDS IN THE PRESENCE OF SIGNIFICANT NOISE", by inventors Alan R. Kahn, et al. This latter invention extracts phase information, rather than amplitude information, from the signals from two spaced-apart microphones, to distinguish blood pressure sound detections from noise.

While complex methods and devices for detecting blood pressure sounds may be used to implement the blood pressure sound detector 34, a simple and low cost blood pressure sound detection method, for providing initial filtering of the microphone signal, is preferably used. The present invention provides the capability for identifying coherent patterns in datasets containing significant artifact data points, thereby making possible the identification of data points representing valid blood pressure sounds to distinguish valid data points of interest from artifact data points. Since the present invention provides the desired noise filtering function, it is not necessary to implement a complex or expensive blood pressure sound detector 34.

It should be noted that the blood pressure sound detector 34 need not be implemented as a component entirely separate from the microprocessor 22. For example, the amplified microphone signal may be digitized, using an analog-to-digital converter, and provided to the microprocessor 22. The microprocessor 22 may then employ a software implemented filtering routine for indicating the detection of a potential blood pressure sound.

The automatic blood pressure monitoring system 10 also includes ECG electrodes 36 attached to the patient's body. The ECG electrodes 36 pick up ECG signals corresponding to the heart beat of the patient 12. The ECG signals are amplified by an amplifier 38 and then provided to an ECG signal detector 40. The ECG signal detector 40 provides a pulse, step, or other signal to the microprocessor 22 in response to the ECG signal. Thus, the ECG signal detector outputs an ECG detection signal at each heart beat. The ECG signal detector 40 may output a pulse in response to any portion of the QRS wave complex of the ECG signal. For example, the ECG signal detector may output a pulse upon the detection of the peak of the R-wave of the ECG signal. The ECG signal detector 40 may thus be implemented using conventional methods for discriminating against noise and other ECG signal components to detect the occurrence of the R-wave peak.

The automatic blood pressure monitoring system 10 is preferably controlled by the system microprocessor 22, or similar programmable digital device. The system microprocessor 22 both controls the blood pressure monitoring cycle and implements the present invention for determining a patient's blood pressure levels. The microprocessor 22 includes an internal clock 42 that is used by the microprocessor 22 to determine the time delay between a signal received from the ECG signal detector 40 and a later signal received from the blood pressure sound detector 34. The system microprocessor 22 is also preferably connected to a system display 44, which may include a monitor, printer, or other conventional display device, for displaying the patient's blood pressure levels and other information as required by a system operator. A user input 46 is also preferably connected to the system microprocessor 22. The user input 46 may include a keyboard, push button, switch, and/or other input devices for initiating a blood pressure monitoring cycle and for inputting patient or operator information into the microprocessor 22. The microprocessor 22 has associated memory 48, e.g., RAM, which may be implemented internal to the microprocessor 22. The microprocessor memory 48 is used in a conventional manner by the microprocessor 22 for storing, for example, patient and operator information input through the user input 46, and cuff pressure and timing information derived from the pressure transducer 24, blood pressure sound detector 34, ECG signal detector 40, and internal clock 42.

The operation of the automatic blood pressure monitoring system 10, employing the present invention to determine a patient's systolic and diastolic blood pressure levels, will now be described. A blood pressure monitoring cycle may be initiated by a system operator using the user input 46. The microprocessor 22 provides control signals on the line 20 to the pressure controller 18 instructing the pressure controller to inflate the inflatable cuff 14 to a pressure level exceeding the maximum probable systolic blood pressure level of the patient 12. At this pressure level, the brachial artery in the patient's arm 16 beneath the cuff 14 is forced closed. Under control of the microprocessor 22, the pressure controller 18 gradually reduces the pressure in the inflatable cuff 14. This may be performed as a continuous or step-wise reduction in the cuff pressure. For example, for each pulse received by the microprocessor 22 from the ECG signal detector 40, the pressure controller may be instructed to reduce the cuff pressure by a small step amount. Thus, the cuff pressure may be reduced in small steps following each heart beat.

When the cuff pressure is reduced below the systolic blood pressure level, the brachial artery beneath the cuff 14 will open and close following each heart beat as the patient's blood pressure first exceeds and then falls below the cuff pressure. The opening of the brachial artery each cycle causes blood pressure sounds to be produced. A blood pressure sound is produced after a delay time following the heart beat. Thus, an ECG detection signal from the ECG signal detector 40 will be followed by a signal from the blood pressure sound detector 34 indicating the detection of a potential blood pressure sound. Some of the potential blood pressure sound detections will correspond to actual blood pressure sounds, others will correspond to noise signals, having characteristics similar to blood pressure sounds, that are passed by the blood pressure sound detector 34. The signals from the blood pressure sound detector 34 and the ECG signal detector 40 may be received as interrupts by the microprocessor 22, or the microprocessor 22 may be programmed to poll the outputs of the blood pressure sound detector 34 and the ECG signal detector 40 at a high rate. The delay time between the signals from the ECG signal detector 40 and the blood pressure sound detector 34 is determined by the microprocessor using the internal clock 42.

The delay time between the potential blood pressure sound detection and the ECG signal detection, along with the corresponding cuff pressure level, determined from the pressure transducer 24, are stored by the microprocessor 22 as a two-dimensional data point in the microprocessor's memory 48. Under steady circumstances, the delay time between the ECG signal and the detection of a blood pressure sound will remain essentially constant. However, as the pressure in the cuff is reduced from the systolic blood pressure level to the diastolic blood pressure level, the time delay will undergo relatively small changes, generally decreasing, but not consistently, on consecutive heart beats as the cuff pressure is gradually reduced. When the cuff pressure is reduced below the patient's diastolic blood pressure level, blood pressure sounds will cease being produced, and the blood pressure cycle may be terminated by rapidly releasing the remaining pressure in the cuff 14.

Figure 2:
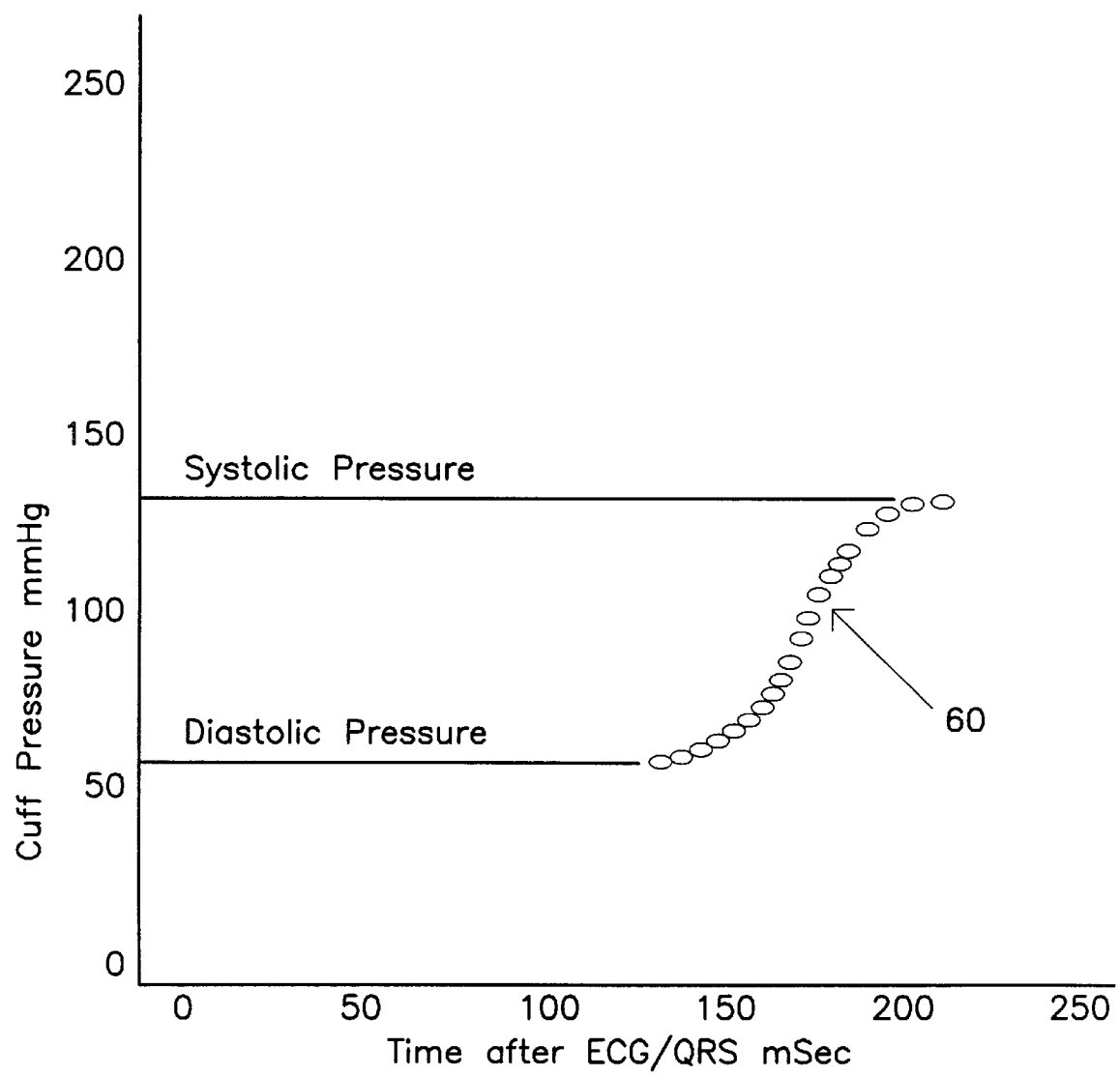
FIG. 2 is a graphical plot of time delay versus cuff pressure for blood pressure sounds detected during a blood pressure measurement cycle.

A graphical plot of two-dimensional data points collected by the microprocessor 22 during a blood pressure monitoring cycle is illustrated in FIG. 2. Each data point is plotted with the time dimension, i.e., the delay time between the ECG signal detection and the blood pressure sound detection, along the x axis, and the magnitude dimension, i.e., the corresponding cuff pressure at the time of each blood pressure sound detection, along the y axis. As can be seen, each data point lies nearby the data points preceding and succeeding it in time and magnitude. Thus, the data points make up a family 60 in that they have a positional relationship with one another in both the time and magnitude dimensions. From this graphical plot, the systolic and diastolic blood pressure levels of a patient can be easily determined. The data point in the family 60 having the highest cuff pressure corresponds to the patient's systolic blood pressure level, and the data point in the family 60 having the lowest cuff pressure corresponds to the diastolic blood pressure level of the patient.

Figure 3:
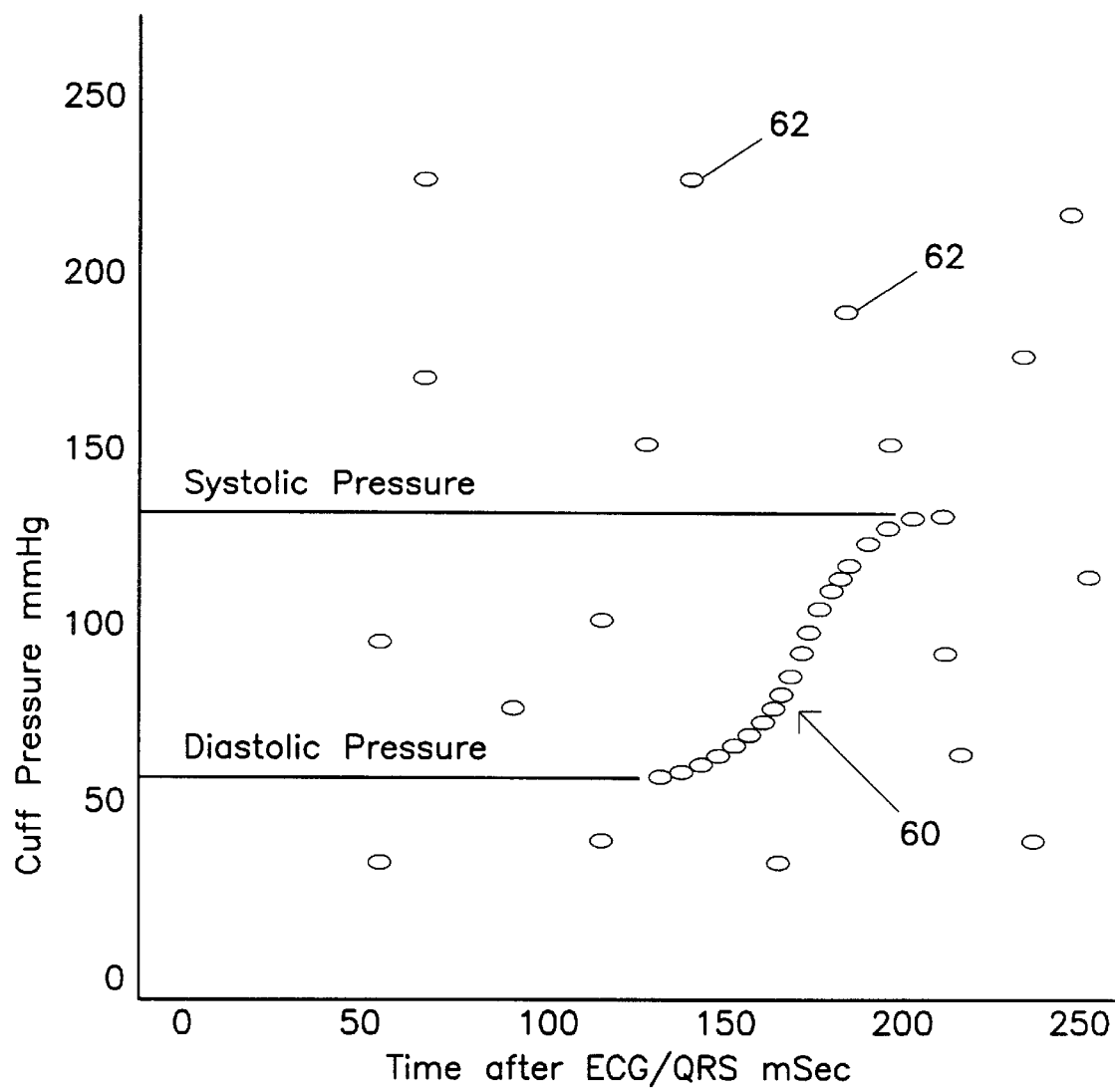
FIG. 3 is a graphical plot of time delay versus cuff pressure for potential blood pressure sounds including blood pressure sounds and random noise artifacts detected during a blood pressure measurement cycle.

To generate the graphical plot of FIG. 2, the blood pressure sound detector 34 would have to produce a pulse only in response to the detection of blood pressure sounds. However, in noisy environments, the blood pressure sound detector 34 is also likely to generate pulses in response to noise and other interference picked up by the microphone 30. This is especially true for noise signals having amplitude and frequency characteristics similar to true blood pressure sounds. The resulting dataset will, therefore, include data points corresponding both to noise detections and blood pressure sound detections. FIG. 3 illustrates the effect of random interference and noise, from the environment or from a patient's body motion, on the data collected during a blood pressure monitoring cycle. As can be seen, in addition to the family 60 of data points corresponding to blood pressure sounds, data points 62 corresponding to noise artifacts are also included in the data set. The systolic and diastolic blood pressure levels of the patient may still be accurately determined from this dataset if the coherent pattern 60, representing valid blood pressure sound detections, can be identified and separated from the artifact data points 62.

Figure 4:
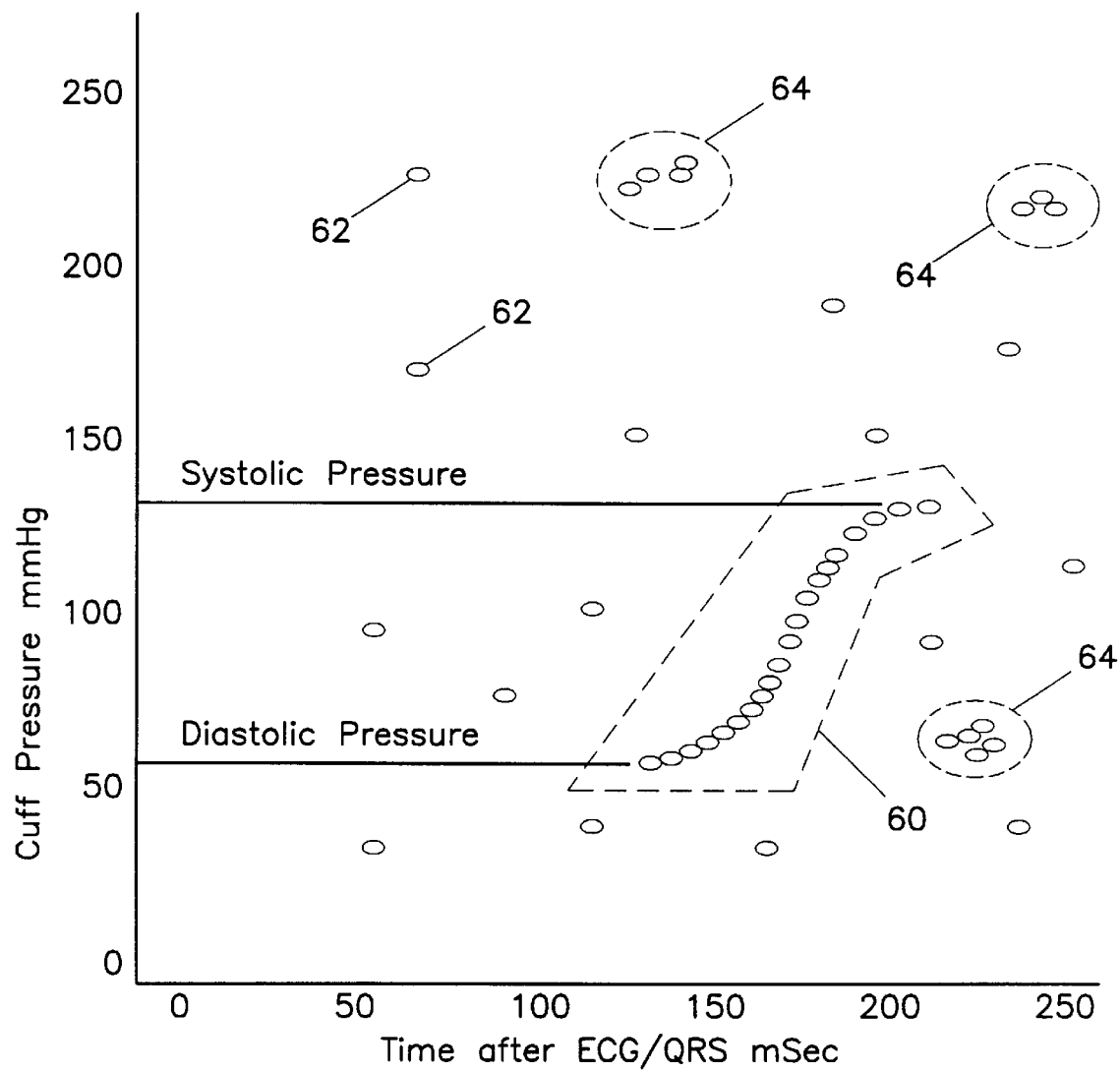
FIG. 4 is a graphical plot of time delay versus cuff pressure for potential blood pressure sounds including blood pressure sounds and noise artifacts detected during a blood pressure measurement cycle in a highly noisy environment, illustrating the grouping of blood pressure sound data points and artifact data points into family groups containing various numbers of data points.

FIG. 4 illustrates the effect of increasing the noise level during the blood pressure monitoring cycle. Under highly noisy conditions, artifact data points are likely to be produced that lie nearby each other in both magnitude and time dimensions. These artifact data points may themselves be combined into families 64. Thus, a dataset generated in a highly noisy measurement environment will include a family of data points 60 corresponding to the dataset of interest, families of artifact data points 64 corresponding to noise, and orphan artifact data points 62, also corresponding to noise. In accordance with the present invention, coherent patterns in a dataset such as that illustrated in FIG. 4 are identified by grouping together closely related data points into families including all data points in the dataset such that each data point in a family has similar time and magnitude dimensions to at least one other data point in the family. Data points not grouped into families are designated as orphans. The family of data points with the largest number of data point members may then be selected as containing the data points of interest. From this selected family of data points, the systolic and diastolic blood pressure levels of a patient may be determined using data points in the selected family of data points at the highest and lowest cuff pressures, respectively.

The present invention may be generalized as follows. A dataset of data points is provided by detecting potential biological/physiological phenomena over several cycles. Each of the data points is a multi-dimensional variable, typically, although not necessarily, including at least a time dimension value and a magnitude dimension value. Thus, for the exemplary application of blood pressure determination, each data point includes a time dimension value corresponding to the time delay between the ECG signal detection and the detection of a potential blood pressure sound, and a magnitude dimension value corresponding to the cuff pressure at the time of the potential blood pressure sound detection. Two points in the dataset are considered "related" to each other, and are thus grouped into the same family, if their values are "similar". For purposes of the present invention, similarity is defined as being "close" to each other in an x-dimensional graph. Thus, for the exemplary application of blood pressure determination, two data points in the data set are considered related if both the time delay and cuff pressure values of the data points are close to each other. One simple check for similarity is, for each dimension, x, two points $d^1_x$ and $d^2_x$ are similar if:

$$|d^1_x - d^2_x| < \text{threshold}_x.$$

$\text{Threshold}_x$ is a number in the x dimension that defines a maximum distance, in that dimension, that the two points can be away from each other and still be related. Thus, for the exemplary application of blood pressure determination, $\text{threshold}_x$ is a time delay threshold in the time dimension and a pressure threshold in the magnitude dimension. Of course, other more complicated similarity functions may also be used.

The grouping of data points into families of similar data points in accordance with the present invention also requires that if data points $d^1$ and $d^2$ are related, and data points $d^2$ and $d^3$ are related, then data points $d^1$ and $d^3$ are related and are grouped in the same family. This must be true even though data points $d^1$ and $d^3$, when compared to each other, would not be considered close to each other on the x dimensional graph. Thus, the present invention requires sorting of the data points in the dataset such that when two data points are found to be closely related, and thus, grouped into the same family, any data points already grouped into a family with either one of those two data points must also be grouped into the family including those two data points.

All related data points that number more than some fixed value define a family. Thus, a family is defined as any group of related data points having at least a selected number of members. The selected number of members must, of course, be at least two, and may be a larger number, preferably three. Data points that are not grouped into families, including all data points that are not closely related to any other data points in the dataset, i.e., all data points in families of size one, are defined as orphan data points.

Figure 5:
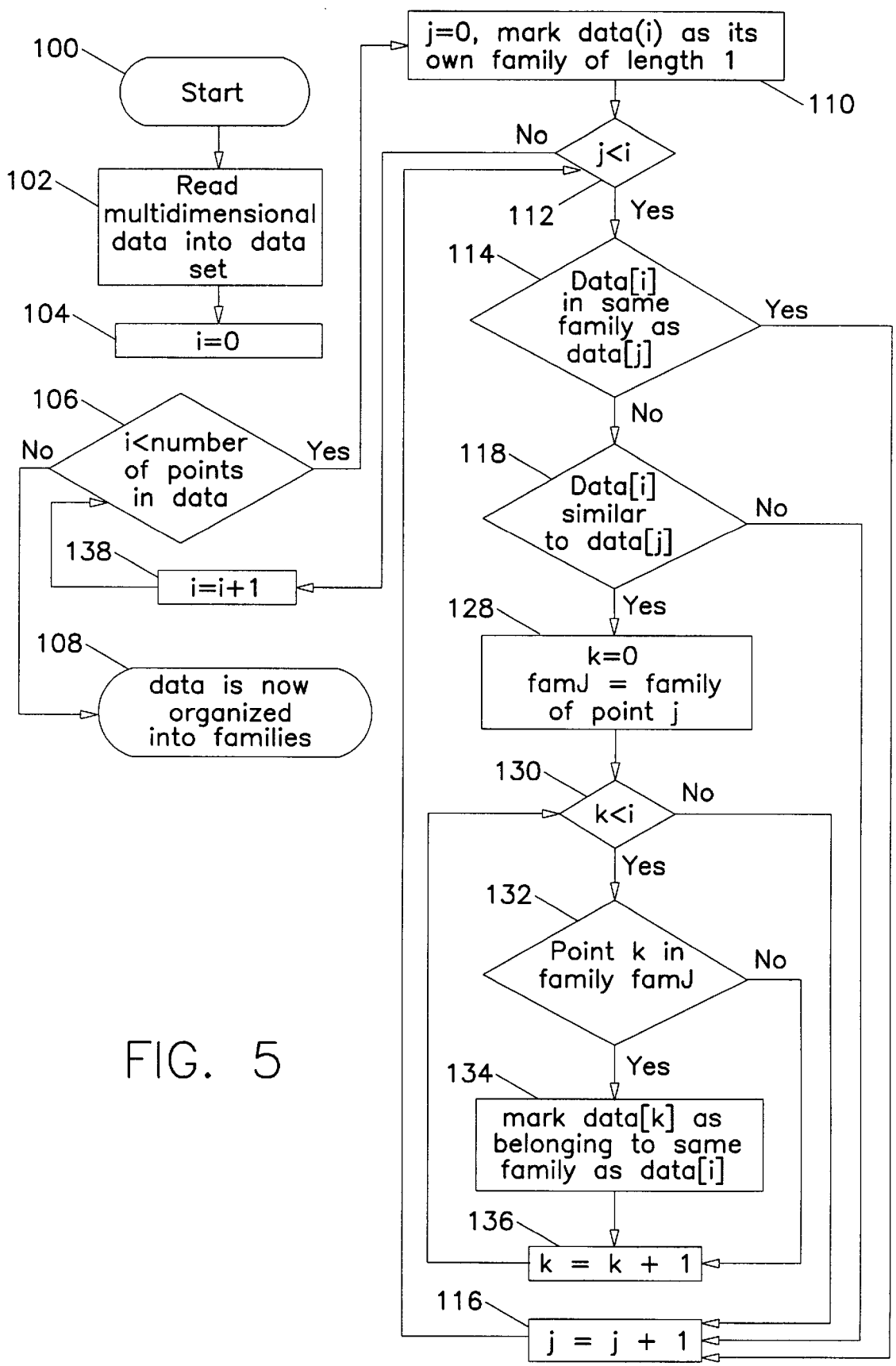
FIG. 5 is a flow chart diagram illustrating the steps of a method in accordance with the present invention for grouping a set of data points into family groups.

A method for grouping data points into families in accordance with the present invention is graphically illustrated by the flow chart diagram of FIG. 5. The algorithm described with respect to FIG. 5 may be implemented as a computer program, to be run on the system microprocessor 22, by a programmer of ordinary skill. It will be apparent that some of the steps in the illustrated algorithm may be performed in an order other than that shown, without adversely affecting the performance of the algorithm or deviating from the invention.

Following the program start 100, the multi-dimensional data points are read into a dataset at step 102. As described previously, for the blood pressure monitoring application of the present invention, data points may be collected in the microprocessor memory 48 point by point as they are obtained during the blood pressure measurement cycle as the cuff 14 is deflated. These exemplary data points are two-dimensional data points, having a time dimension value corresponding to the delay between the ECG detection signal and the potential blood pressure sound detection signal, and a magnitude dimension value corresponding to the cuff pressure at the time of the potential blood pressure sound detection. Note that the order in which data points are read into the data set is irrelevant. Thus, for the blood pressure measurement application, data points representing potential blood pressure sound detections may be added to the data set when the cuff is being inflated, as well as when it is being deflated. If the patient moves the arm on which the cuff is placed, the cuff will undergo potentially wide pressure fluctuations. Potential blood pressure sound detections will be generated during these pressure fluctuations. The resulting "out of order" data points generated are also added to the data set for processing by the present invention. These data points may contain valid blood pressure sound detections that will be used to fill out the coherent pattern that is to be identified. What is important is that many potential blood pressure sound detection data points be included in the data set for a range of cuff pressures extending from above the maximum probable systolic blood pressure level of the patient to below the minimum probable diastolic blood pressure level of the patient.

Multi-dimensional data points may be stored in the memory 48 using a conventional data structure such that, for example, data[n] refers to the nth data point in the dataset. At step 104, a variable i is set equal to zero. At step 106, a check is made to determine whether the variable i is less than the number of data points in the dataset. If i is not less than the number of data points in the dataset, then each data point in the dataset has been considered and the entire dataset has been organized into families and orphans. Thus, a negative response at step 106 indicates that the grouping of the dataset is complete, and the algorithm is terminated at step 108.

If the variable i is less than the number of data points in the dataset, then there are data points that have yet to be considered, so the algorithm will proceed to step 110. At step 110, a second variable j is set equal to zero, and the data point data[i] is assigned to its own family of length 1. At step 112, a determination is made whether variable j is less than variable i. If the answer to step 112 is yes, the algorithm proceeds to step 114. At step 114, a determination is made whether data point data[i] has already been grouped in the same family as data point data[j]. If this is the case, the algorithm proceeds to step 116 wherein the variable j is incremented.

Figure 6:
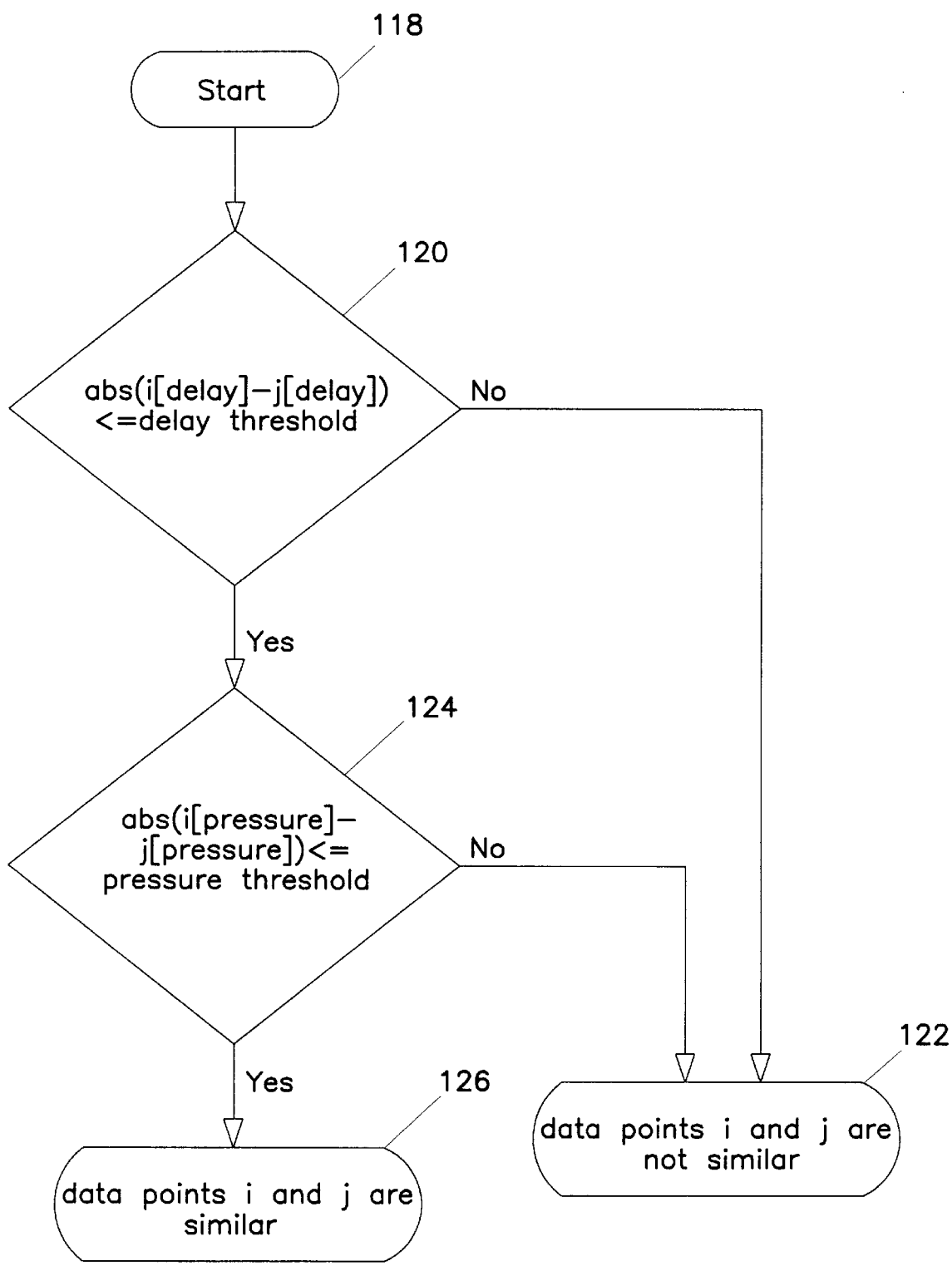
FIG. 6 is a flow chart diagram illustrating the steps of a two-dimensional similarity function used for determining the similarity of and grouping potential blood pressure sound data points into family groups in accordance with the method of the present invention.

If data point data[i] is not in the same family as data point data[j], a calculation is performed at step 118 to determine whether data point data[i] is similar to data point data[j]. For the exemplary application of the present invention to blood pressure monitoring, this determination may be made using the algorithm described graphically by the flow chart of FIG. 6. For this application, the two dimensional data points include a time dimension value corresponding to the delay time between the ECG detection signal and the potential blood pressure sound detection signal, and a magnitude dimension value corresponding to the cuff pressure at the time of the potential blood pressure sound detection. Step 118 determines the similarity of two data points by comparing the differences between the dimension values of the two data points to selected threshold levels. In step 120, the absolute value of the difference between the delay time dimension values of each data point is compared to a time threshold. If the absolute value of the difference of the two data point values in this dimension exceeds a time delay threshold value, the data points are determined to be not similar 122 and step 118 returns a negative response. However, if the absolute value of the difference between the data point values in the time dimension meets the time dimension threshold, the algorithm proceeds to step 124 wherein the similarity of the magnitude dimension values of the two data points is determined. Thus, at step 124, the absolute value of the difference between the magnitude dimension values of the two data points is compared to a pressure threshold value. If the difference between the two magnitude dimension values exceeds the pressure threshold, the two data points are determined to be not similar 122 and step 118 produces a negative result. However, if both dimensional values, time and magnitude, are determined to meet their respective threshold values, the two data points are determined to be similar 126, step 118 produces a positive result, and the algorithm proceeds to step 128. If the result of step 118 is negative, the algorithm proceeds to step 116 wherein the variable j is incremented. It is apparent that the effect of steps 114 and 118 of the algorithm may be summarized generally as follows. Two data points, data[i] and data[j] are considered. If the two data points are already members of the same family, step 114, or the data points are not similar, step 118, then no further action needs to be taken with respect to these two data points. Thus, the program proceeds to consider another pair of data points, by incrementing the variable j, if the result of step 114 is positive or the result of step 118 is negative.

If the result of step 118 is positive, then two data points not yet grouped in the same family have been found to be similar. These two data points must be grouped into the same family. At step 128, a variable k is set equal to zero and a variable famJ is set equal to the family containing data point data[j]. At step 130, a determination is made whether the variable k is less than the variable i. If the answer to step 130 is positive, a determination is made at step 132 whether data point data[k] is in the family famJ. If this is the case, data point data[k] is grouped into the same family with data point data[i] at step 134, and the variable k is incremented at step 136. If the result of step 132 is negative, and data point data[k] is not in the family famJ, step 134 is bypassed and variable k is incremented at step 136. This process is repeated until k is equal to i, at which point the result of step 130 is negative, and the algorithm proceeds to step 116 where variable j is incremented. It is apparent that the effect of steps 128–136 of the algorithm is, after having determined that data point data[i] is similar to data point data[j] in step 118, to group data point data[i] into the same family as data point data[j], along with any other data points that have already been grouped into a family with data point data[j].

After variable j is incremented at step 116, steps 112–136 are repeated, as required, for consecutive values of variable j until the result of step 112 is negative. At this point, the algorithm proceeds to step 138 wherein the variable i is incremented, and step 106 wherein the incremented value of i is compared to the number of data points in the dataset. The processing of additional data points is continued at step 110 if the result of step 106 is positive. The algorithm is completed 108, with all of the data points in the dataset being grouped into families and orphans, if the result of step 106 is negative. It is apparent that the effect, in summary, of the algorithm illustrated in FIG. 5, is to consider each data point in the dataset in sequence, determine the similarity between that data point and all previously considered data points, and group two data points that are found to be similar into the same family, including in the family all data points in a family into which the previously considered data point has already been grouped. This results in the grouping of the data points in the dataset into families of data points such that each data point in the family has similar dimensional values to at least one other data point included in the family.

For the blood pressure monitoring application, the grouping of data points is preferably accomplished each time a new data point is added to the dataset. After each run of the algorithm, in the event that three or more closely related data points are grouped into a family, the data points in this family are displayed in a two-dimensional plot on the system display 44. If subsequently generated data points are closely related to any points in this family, they will be added to the family group during subsequent runs of the algorithm. These additional data points are preferably added to the plot on the display 44 as the family size is increased. During the blood pressure monitoring cycle, as the cuff 14 is being deflated (or inflated), other families including three or more data points may also be grouped by the algorithm. Data points in these families are preferably not plotted on the display 44 unless the number of related data points included in the family exceeds the number of data points in the family already displayed on the display 44. At such point, the plot of the family of data points displayed on the display 44 is erased, and is replaced by a plot of the data points in the family containing the larger number of data points. In this manner, by the time the cuff deflation is completed, at the end of the blood pressure monitoring cycle, only data points included in the family having the largest number of data points will remain displayed on the display 44.

In a typical blood pressure monitoring cycle, the coherent data pattern corresponding to detections of valid blood pressure sounds may typically include 15–20 data points. Even in cases of severe noise interference, families of closely related artifact data points, arising from noise, will typically include less than five data points. Thus, the data points of interest will almost always be included in the prevailing family containing the largest number of data points. At the end of the blood pressure monitoring cycle, the highest and lowest pressure levels of data points in the family including the largest number of data points may be used, respectively, to determine the systolic and diastolic blood pressure levels of the patient 12. The identification of coherent patterns in non-stationary periodic data in accordance with the present invention is thus used to identify data points corresponding to true blood pressure sound detections, in the presence of high levels of random interference and noise, thereby providing for the accurate determination of a patient's systolic and diastolic blood pressure levels.

The set of data points of interest, corresponding to true blood pressure sound detections, may be used for applications other than the determination of a patient's systolic and diastolic blood pressure levels. For example, the systolic slope of the blood pressure wave in a patient's artery may be easily derived from the identified data points of interest. From characteristics of the systolic slope, various conditions such as valvular heart disease, myocardial heart disease, metabolic diseases which affect cardiac function, and thyroid dysfunctions may be diagnosed.

Figure 7:
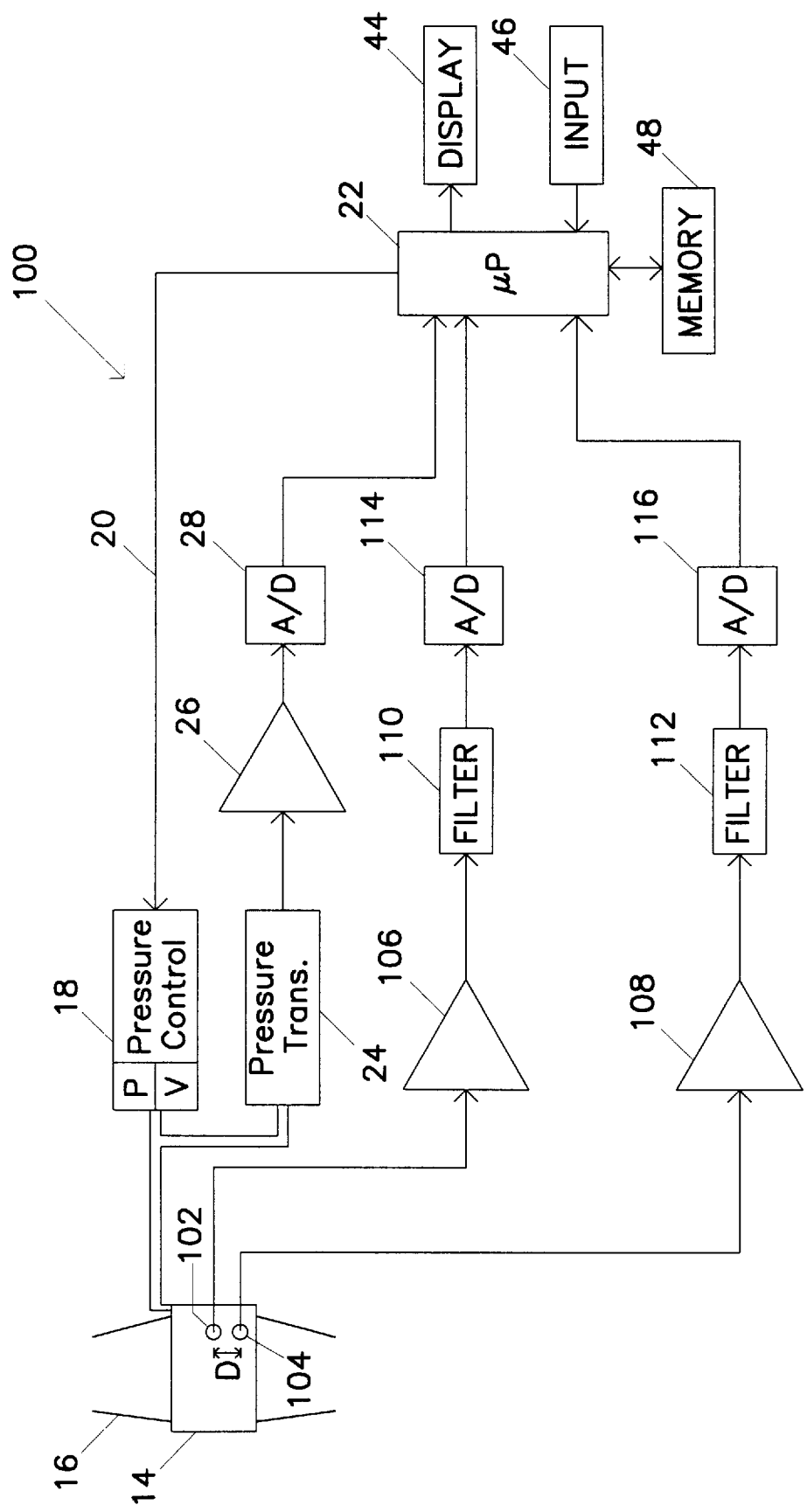
FIG. 7 is a schematic block diagram of an automatic blood pressure monitoring system employing coherent pattern identification in accordance with an alternative embodiment of the present invention.

An automatic blood pressure monitoring system 100 employing coherent pattern identification in accordance with an alternative embodiment of the present invention is described with reference to the schematic block diagram of FIG. 7. Components of the alternative automatic blood pressure monitoring system 100 having the same basic function and structure as components in the automatic blood pressure monitoring system 10 of FIG. 1 are labeled with the same reference numerals in FIG. 7. This alternative embodiment of the present invention is presented to illustrate how non-stationary periodic data derived from other physiological phenomena measurements may be grouped into families in accordance with the present invention, to thereby accurately determine a patients' systolic and diastolic blood pressure levels.

In the blood pressure monitoring system 100, two microphones 102 and 104 are fixed in the inflatable cuff 14, which is wrapped around the arm 16 of the patient. The microphones 102 and 104 are placed apart by a distance D, e.g., approximately 2–3 centimeters, such that a low frequency blood pressure sound propagating down the arm 16 will be picked up out of phase, preferably by approximately 180°, by each microphone 102 and 104. Note that a noise signal, traveling at the speed of sound, will generally be picked up simultaneously and in-phase by each microphone 102 and 104. The signals from the two microphones are amplified 106 and 108, filtered to extract frequency components from the microphone signals that are known to correspond to blood pressure sounds, e.g., using band pass filters 110 and 112 having pass bands of approximately 30–80 Hz, and converted to digital signals by analog-to-digital converters 114 and 116, respectively. The digitized microphone signals from the analog-to-digital converters 110 and 112 are provided to the microprocessor 22 which derives multi-dimensional data points therefrom.

In the manner described previously, the cuff 14 is inflated and deflated through various cuff pressures, extending from above the systolic blood pressure level of the patient to below the diastolic blood pressure level of the patient, by the pressure controller 18, under control of the microprocessor 22. At each pressure level, the corresponding cuff pressure, determined from the pressure transducer 24, is recorded in memory 48 by the microprocessor 22, along with a multi-dimensional data point derived from the signals from the two microphones 102 and 104.

Figure 8:
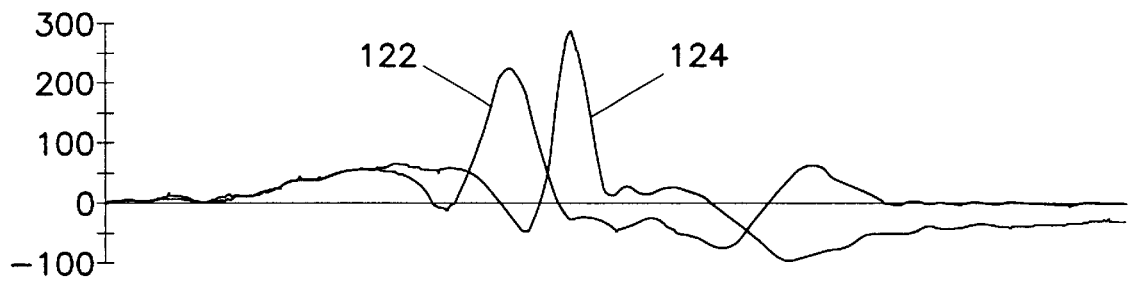
FIGS. 8–11 are graphs of exemplary microphone signal waveforms produced by the blood pressure monitoring system of FIG. 7 and from which three-dimensional data points are derived.
Figure 9:
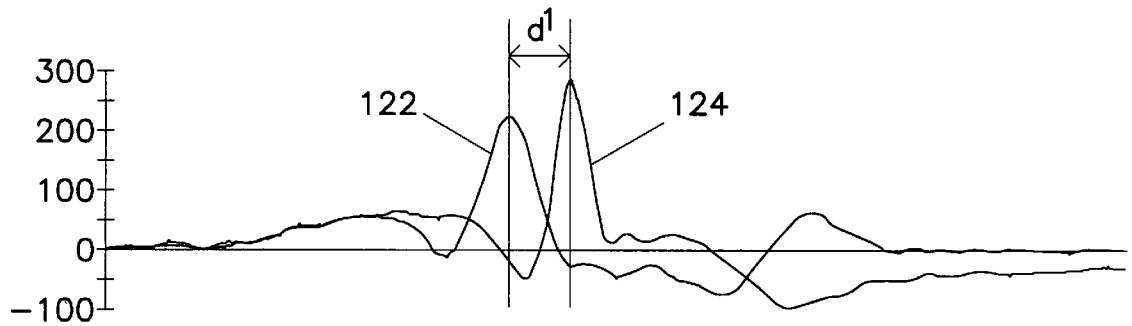
Figure 10:
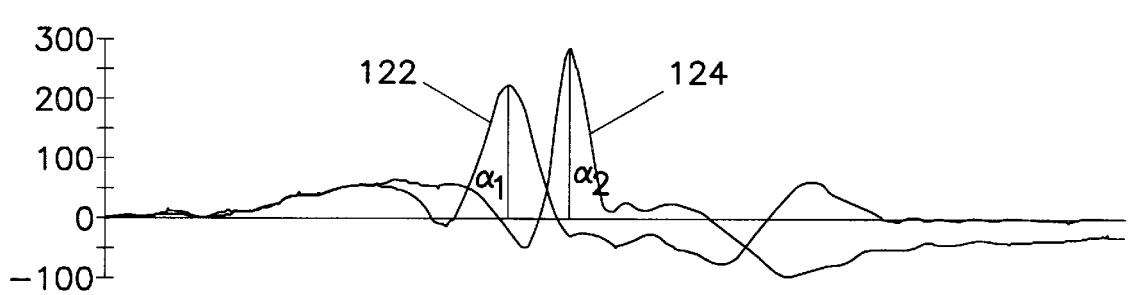
Figure 11:
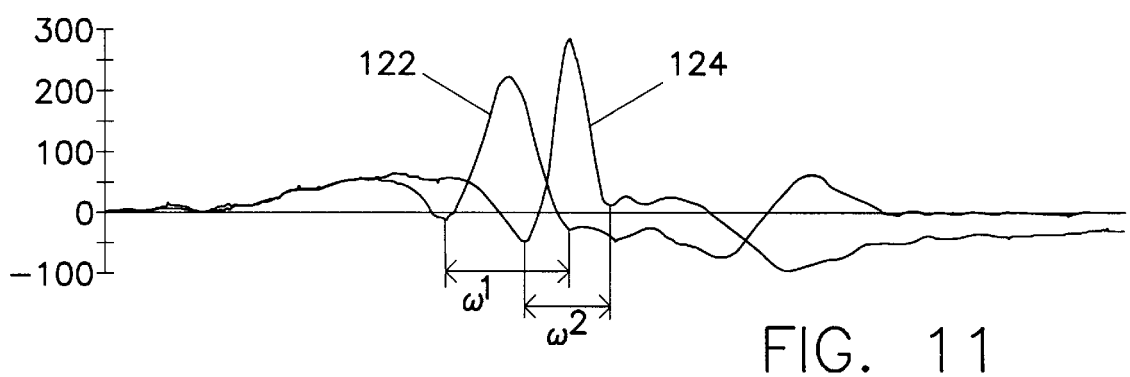

Two exemplary and typical microphone signals 122 and 124 are illustrated in FIG. 8. Each microphone signal 122 and 124 includes a signal pulse corresponding to a low frequency blood pressure sound picked up by the microphones 102 and 104, respectively. Note that the pulses are separated in time and have different wave shapes. These pulse characteristics will change gradually with respect to different cuff pressures, forming a coherent pattern of non-stationary periodic data that can be identified in accordance with the present invention to distinguish microphone signals resulting from blood pressure sound detections from noise signals. This is accomplished by first mapping the two microphone signal waveforms into a multi-dimensional data point for each pair of microphone signal pulses detected at each cuff pressure level. As illustrated in FIG. 9, the first dimension value $d^1$ may be set equal to the distance (in time) between the peaks of the first microphone signal 122 and the second microphone signal 124. As illustrated in FIG. 10, the second dimension value $d^2$ may be set equal to the ratio of amplitude $a_1$ of the first microphone signal 122 to amplitude $a_2$ of the second microphone signal 124. Thus, $d_2=a_1/a_2$. As illustrated in FIG. 11, the third dimension value $d^3$ may be set equal to the ratio of the width $w_1$ of the peak of the first microphone signal 22 to the width $w_2$ of the peak of the second microphone signal 124. Thus, $d^3=w_1/w_2$. The widths $w_1$ and $w_2$ may be computed by determining the points to the left and right of each microphone signal peak where the slope goes to zero and reverses itself. This width is, in effect, approximately one-half of the wavelength. Note that, under this mapping, dimension values $d^1$ and $d^3$ are time dimension values and dimension value $d^2$ is a magnitude dimension value.

Using the method of grouping data points into families in accordance with the present invention, three dimensional data points derived from the two microphone signals at various cuff pressures, and having similar dimensional values, may be grouped together into the same family. Two three-dimensional data points $p_1$ and $p_2$ may be defined as related, and hence grouped into the same family, if:

|  | | |
|---|---|---|
|  | $\|p_1(d^1) - p_2(d^1)\|$ | < time threshold |
| AND | $\|p_1(d^2) - p_2(d^2)\|$ | < amplitude threshold |
| AND | $\|p_1(d^3) - p_2(d^3)\|$ | < width threshold. |

The data points that are grouped into the family of data points including the largest number of data points may then be used to determine the patients' systolic and diastolic blood pressure levels from, for example, the highest and lowest cuff pressure levels associated with data points in the largest family, respectively. Data points derived from microphone signal pulses resulting from noise will be distributed throughout the three dimensional space and will, therefore, either be grouped into small families or not grouped at all, and will, therefore, not effect the determination of the patient's blood pressure.

It is understood that this invention is not limited to the particular embodiments and applications illustrated and described herein, but embraces all such modified forms thereof as come within the scope of the following claims.

What is claimed is:

1. A method for identifying blood pressure sounds of a patient, comprising the steps of:
   (a) applying a plurality of pressure levels to an artery of the patient;
   (b) detecting the pressure applied at each of the plurality of pressure levels;
   (c) detecting a patient ECG signal at each of the plurality of pressure levels;
   (d) detecting a potential blood pressure sound at each of the plurality of pressure levels;
   (e) determining a time delay between the detections of the ECG signal and the potential blood pressure sound;
   (f) generating a two dimensional data point at each of the plurality of pressure levels, a time dimension value of the data point corresponding to the time delay between the detected patient ECG signal at the pressure level and the detected potential blood pressure sound at the pressure level and a magnitude dimension value of the data point corresponding to the detected pressure at the pressure level, the two dimensional data points generated at each of the pressure levels forming a data set;
   (g) grouping the data points in the data set into families by grouping together data points from the data set such that each data point in a family has similar time and magnitude dimension values to at least one other data point included in the family; and
   (h) selecting the data points in the family of data points that includes the largest number of data points as the set of data points of interest identifying blood pressure sounds.

2. The method of claim 1 comprising additionally the step of determining a patient's blood pressure from the data points of interest, including the steps of determining the patients's systolic blood pressure level based on the pressure level of a data point in the set of data points of interest having a largest pressure level dimension value and determining the patient's diastolic blood pressure level based on a detected pressure level of a data point in the set of data points of interest having a smallest pressure level dimension value.

3. The method of claim 1 wherein the step of applying a plurality of pressure levels to an artery of the patient includes the steps of:
   (a) wrapping an inflatable cuff around an upper arm of the patient;
   (b) inflating the cuff to a pressure level exceeding the systolic blood pressure level of the patient; and
   (c) gradually deflating the cuff to a cuff pressure less than the diastolic blood pressure level of the patient to apply the plurality of blood pressure levels to an artery in the arm of the patient.

4. The method of claim 1 wherein the step of applying a plurality of pressure levels to an artery of the patient includes the steps of:
   (a) wrapping an inflatable cuff around an upper arm of the patient; and
   (b) gradually inflating the cuff from a cuff pressure level below the diastolic blood pressure level of the patient to a cuff pressure level above the systolic blood pressure level of a patient to apply the plurality of pressure levels to an artery in the arm of the patient.

5. The method of claim 1 wherein the step of detecting a potential blood pressure sound includes the steps of placing a microphone on the patient over the artery, the microphone producing a microphone signal in response to blood pressure sounds and noise picked up by the microphone, and processing the microphone signal to generate a potential blood pressure sound detection signal in response to microphone signals produced in response to blood pressure sounds and noise that is similar to blood pressure sounds.

6. The method of claim 1 wherein the step of grouping data points in the data set into families includes the step of determining if two data points are similar by comparing the absolute value of the difference between the time dimension values of the data points with a time delay threshold value and comparing the absolute value of the difference between the magnitude dimension values of the data points with a pressure threshold value.

7. The method of claim 1 wherein a family of data points includes at least three data points such that each data point in the family has similar time and magnitude dimension values to at least one other data point included in the family.

8. The method of claim 1 including the additional steps of:
   (a) repeating the step of grouping the data points in the data set into families each time a data point is added to the data set; and
   (b) displaying a two dimensional plot of the data points in the family including the largest number of data points.

9. An apparatus for measuring the blood pressure of a patient, comprising:
   (a) means for applying a plurality of pressure levels to an artery of the patient;
   (b) means for detecting the pressure applied at each of the plurality of pressure levels;
   (c) means for detecting a patient ECG signal at each of the plurality of pressure levels;
   (d) means for detecting a potential blood pressure sound at each of the plurality of pressure levels;
   (e) means for determining a time delay between the detections of the ECG signal and the potential blood pressure sound;
   (f) means for generating a two dimensional data point at each of the plurality of pressure levels, a time dimension value of the data point corresponding to the time delay between the detected patient ECG signal at the pressure level and the detected potential blood pressure sound at the pressure level and a magnitude dimension value of the data point corresponding to the detected pressure level, the two dimensional data points generated at each of the pressure levels forming a data set;
   (g) means for grouping the data points in the data set into families by grouping together data points from the data set such that each data point in a family has similar time and magnitude dimension values to at least one other data point included in the family;
   (h) means for selecting the data points in the family of data points that includes the largest number of data points as the set of data points of interest; and
   (i) means for determining the patient's blood pressure from the data points of interest.

10. The apparatus for measuring blood pressure of claim 9 wherein the means for determining the patient's blood pressure includes means for determining the patients's systolic blood pressure level based on the detected pressure level of a data point in the set of data points of interest having a largest pressure level dimension value and for determining the patient's diastolic blood pressure level based on a detected pressure level of a data point in the set of data points of interest having a smallest pressure level dimension value.

11. The apparatus for measuring blood pressure of claim 9 wherein the means for applying a plurality of pressure levels to an artery of the patient includes:

(a) an inflatable cuff;

(b) means for inflating the cuff to a pressure level exceeding the systolic blood pressure level of the patient; and (c) means for gradually deflating the cuff to a cuff pressure less than the diastolic blood pressure level of the patient to apply the plurality of blood pressure levels to an artery in the arm of the patient.

12. The apparatus for measuring blood pressure of claim 9 wherein the means for applying a plurality of pressure levels to an artery of the patient includes:

(a) an inflatable cuff;

(b) means for gradually inflating the cuff from a cuff pressure level below the diastolic blood pressure level of the patient to a cuff pressure level above the systolic blood pressure level of a patient to apply the plurality of pressure levels to an artery in the arm of the patient.

13. The apparatus for measuring blood pressure of claim 9 wherein the means for detecting the pressure applied at each of the plurality of pressure levels includes a pressure transducer.

14. The apparatus for measuring blood pressure of claim 9 wherein the means for detecting a potential blood pressure sound includes a microphone placed on the patient over the artery, the microphone producing a microphone signal in response to blood pressure sounds and noise picked up by the microphone, and means for processing the microphone signal to generate a potential blood pressure sound detection signal in response to microphone signals produced in response to blood pressure sounds and noise that is similar to blood pressure sounds.

15. The apparatus for measuring blood pressure of claim 9 wherein the means for grouping data points in the data set into families includes means for determining if two data points are similar by comparing the absolute value of the difference between the time dimension values of the data points with a time delay threshold value and comparing the absolute value of the difference between the magnitude dimension values of the data points with a pressure threshold value.

16. The apparatus for measuring blood pressure of claim 9 wherein the means for grouping the data points in the data set into families includes a digital microprocessor implementing an algorithm for grouping the data points.

17. The apparatus for measuring blood pressure of claim 9 including a display device and means for displaying a two dimensional plot of the data points in the family including the largest number of data points on the display device.

18. A method for making biological measurements, comprising the steps of:

(a) making detections of potential non-stationary periodic biological phenomena over a plurality of cycles;

(b) generating a multi-dimensional data point at each of the plurality of cycles, each data point including at least a time dimension value of the data point corresponding to a time dimension of the potential phenomenon detection and a magnitude dimension value of the data point corresponding to a magnitude dimension of the potential phenomenon detection, the multi-dimensional data points generated at each of the plurality of cycles forming a data set;

(c) grouping the data points in the data set into families by grouping together data points from the data set such that each data point in a family has similar time and magnitude dimension values to at least one other data point included in the family;

(d) selecting the data points in the family of data points that includes the largest number of data points as the set of data points of interest; and (e) making a biological measurement from the data points of interest.

19. The method of claim 18 wherein the potential non-stationary periodic biological phenomena include ECG signals and blood pressure sounds produced by the opening of a patient's artery to which a plurality of pressure levels are applied, wherein the time dimension value of the potential non-stationary periodic biological phenomenon detection includes a time delay between the detection of the ECG signal and the detection of the blood pressure sound at each pressure level, wherein the magnitude dimension value of the potential non-stationary periodic biological phenomenon detection includes the pressure level, and wherein the biological measurement made from the data points of interest includes systolic and diastolic blood pressure levels of a patient.

20. The method of claim 18 wherein the step of grouping data points in the data set into families includes the step of determining if two data points are similar by comparing the absolute value of the difference between the time dimension values of the data points with a time dimension threshold value and comparing the absolute value of the difference between the magnitude dimension values of the data points with a magnitude dimension threshold value.

21. The method of claim 18 wherein a family of data points includes at least three data points such that each data point in the family has similar time and magnitude dimension values to at least one other data point included in the family.

22. The method of claim 18 wherein the potential non-stationary periodic biological phenomena include pulse waveform signals produced by the opening of a patient's artery to which a plurality of pressure levels are applied and which are detected out of phase by two separated microphones placed on the patient over the artery, wherein a multi-dimensional data point generated at each pressure level includes a time dimension value corresponding to a distance in time between peaks of the pulse waveform signals detected by each microphone, a magnitude dimension value corresponding to a ratio of amplitudes of the pulse waveform signals detected by each microphone, and a time dimension value corresponding to a ratio of widths of the pulse waveform signals detected by each microphone, and wherein the biological measurement made from the data points of interest includes systolic and diastolic blood pressure levels of the patient.

* * * * *